(12) United States Patent
Raje et al.

(10) Patent No.: US 11,998,739 B2
(45) Date of Patent: Jun. 4, 2024

(54) MONOLITHIC COMPONENT FOR AN IMPLANTABLE MEDICAL DEVICE

(71) Applicant: Cochlear Limited, Macquarie University (AU)

(72) Inventors: Milind Chandrakant Raje, Macquarie University (AU); Martin Joseph Svehla, Macquarie University (AU); Charles Roger Leigh, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 102 days.

(21) Appl. No.: 17/117,753

(22) Filed: Dec. 10, 2020

(65) Prior Publication Data

US 2021/0093861 A1 Apr. 1, 2021

Related U.S. Application Data

(63) Continuation of application No. 15/648,094, filed on Jul. 12, 2017, now abandoned.

(51) Int. Cl.
| | |
|---|---|
| *A61N 1/05* | (2006.01) |
| *A61F 2/18* | (2006.01) |
| *A61N 1/36* | (2006.01) |
| *A61N 1/375* | (2006.01) |
| *H04R 25/00* | (2006.01) |

(52) U.S. Cl.
CPC .............. *A61N 1/3603* (2017.08); *A61F 2/18* (2013.01); *A61N 1/0541* (2013.01); *A61N 1/36038* (2017.08); *A61N 1/375* (2013.01); *A61F 2002/183* (2013.01); *H04R 25/606* (2013.01); *H04R 2460/13* (2013.01)

(58) Field of Classification Search
CPC ... A61N 1/0541; A61N 1/36038; A61N 1/375
See application file for complete search history.

(56) References Cited

U.S. PATENT DOCUMENTS

| | | | |
|---|---|---|---|
| 8,055,058 | B2 | 11/2011 | Moon et al. |
| 9,144,676 | B2 | 9/2015 | Gibson |

(Continued)

FOREIGN PATENT DOCUMENTS

| | | |
|---|---|---|
| KR | 10-1393186 B1 | 5/2014 |
| WO | 2010085838 A1 | 8/2010 |

(Continued)

OTHER PUBLICATIONS

International Search Report and Written Opinion for Application No. PCT/IB2018/000895 dated Jan. 2, 2019.

(Continued)

*Primary Examiner* — Eric D. Bertram
(74) *Attorney, Agent, or Firm* — Edell, Shapiro & Finnan, LLC

(57) ABSTRACT

A monolithic implantable medical device component includes multiple portions on a single substrate. The portions can be electrically connected to an electronics module, which may include output connectors and input connectors to and from the various portions of the substrate. A portion of the monolithic component to be disposed within, attached to, embedded in, or otherwise combined with a magnet retention feature, such as a plate.

25 Claims, 10 Drawing Sheets

(56) References Cited

U.S. PATENT DOCUMENTS

| | | | |
|---|---|---|---|
| 9,220,907 B2 * | 12/2015 | Mashiach | A61N 1/0526 |
| 10,058,702 B2 | 8/2018 | Gibson | |
| 10,130,807 B2 | 11/2018 | Leigh | |
| 10,232,171 B2 | 3/2019 | Gibson | |
| D849,740 S | 5/2019 | Malouf | |
| 10,576,276 B2 | 3/2020 | Leigh | |
| 10,674,287 B2 | 6/2020 | Leigh | |
| 2009/0250253 A1 | 10/2009 | Park | |
| 2010/0274313 A1 * | 10/2010 | Boling | A61N 1/37217 607/116 |
| 2013/0237906 A1 | 9/2013 | Park | |
| 2015/0025613 A1 | 1/2015 | Nyberg, II | |
| 2016/0361537 A1 * | 12/2016 | Leigh | A61N 1/36038 |
| 2017/0056646 A1 * | 3/2017 | Sibary | A61N 1/0541 |
| 2019/0076661 A1 | 3/2019 | Dhanasingh | |

FOREIGN PATENT DOCUMENTS

| | | |
|---|---|---|
| WO | 2016127130 A1 | 8/2016 |
| WO | 2017029615 A1 | 2/2017 |

OTHER PUBLICATIONS

Jeong et al., "Liquid Crystal Polymer (LCP), an Attractive Substrate for Retinal Implant," Sensors and Materials, 24(4):189-203, 2012.
Lawrence Livermore National Laboratory, "Artificial Retina (past)" Retrieved from the Internet: <URL: hllps://neurotech.lnl.gov/projects/artificial-retina>. Retrieved Apr. 25, 2017, 2 pages.

* cited by examiner

MONOLITHIC COMPONENT FOR AN IMPLANTABLE MEDICAL DEVICE

CROSS REFERENCE TO RELATED APPLICATIONS

This application is a continuation of U.S. application Ser. No. 15/648,094, filed on Jul. 12, 2017, and entitled, "Monolithic Component For An Implantable Medical Device," the contents of which are hereby incorporated by reference in their entirety.

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate their auditory nerves in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a recipient experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Monolithic implantable medical device components are disclosed. For example, in one embodiment, a monolithic component for a medical device includes a substrate. Various components or regions can be formed on the substrate, including a telemetry coil, an electrical interface region, and a region for interfacing with recipient anatomy and acting as a stimulator or a sensor.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The technologies described herein can typically be used with medical devices, such as auditory prostheses (e.g., cochlear implants). Traditionally, medical devices have separately-made components (e.g., coils, electrodes, and connection parts) that are then assembled to form the medical device. This approach can create a number of connection interfaces and can lead to significant handling during manufacture. As a result, these medical devices can have complex fabrication processes and reliability concerns.

Many disclosed embodiments can address one or more drawbacks of traditional devices and systems. For example, a number of disclosed embodiments can include a monolithic implantable medical device component having a variety of portions (e.g., a coil portion, an anatomy interface portion, an electrical interface region, etc.); this arrangement can reduce the number of connection interfaces, allow for improved reliability due to the reduced number of interfaces, as well as allow for more efficient and easier manufacturing.

Many disclosed embodiments can further allow for improvements to implantable devices that use one or more plates or other components to resist movement of magnets, such as when subject to magnetic resonance imaging (MRI). Examples of such devices are described in US Patent Application Publication No. 2016/0361537A1, filed Jan. 29, 2016, incorporated herein by reference in its entirety for any and all purposes and specifically with regard to the integration of plates to inhibit movement by an incorporated retention magnet (e.g. when exposed to MM). Certain disclosed embodiments can allow for a coil portion of a monolithic implantable medical device component to be disposed within, attached to, embedded in, or otherwise combined with such a plate; in several embodiments, a coil portion can act as the plate. This can further simplify assembly. Further, it can allow a coil to be placed in such a manner as to minimize the distance between the coil (once implanted) and a corresponding external coil of an associated external medical device thereby increasing efficiency of signal transfer between the coils. Combining the coil and the plate can further allow for additional flexibility in removing the magnet. For example, the magnet can be removed in a direction parallel to the diameter of the coil, as discussed in more detail with regard to FIG. 7.

Figure 1:
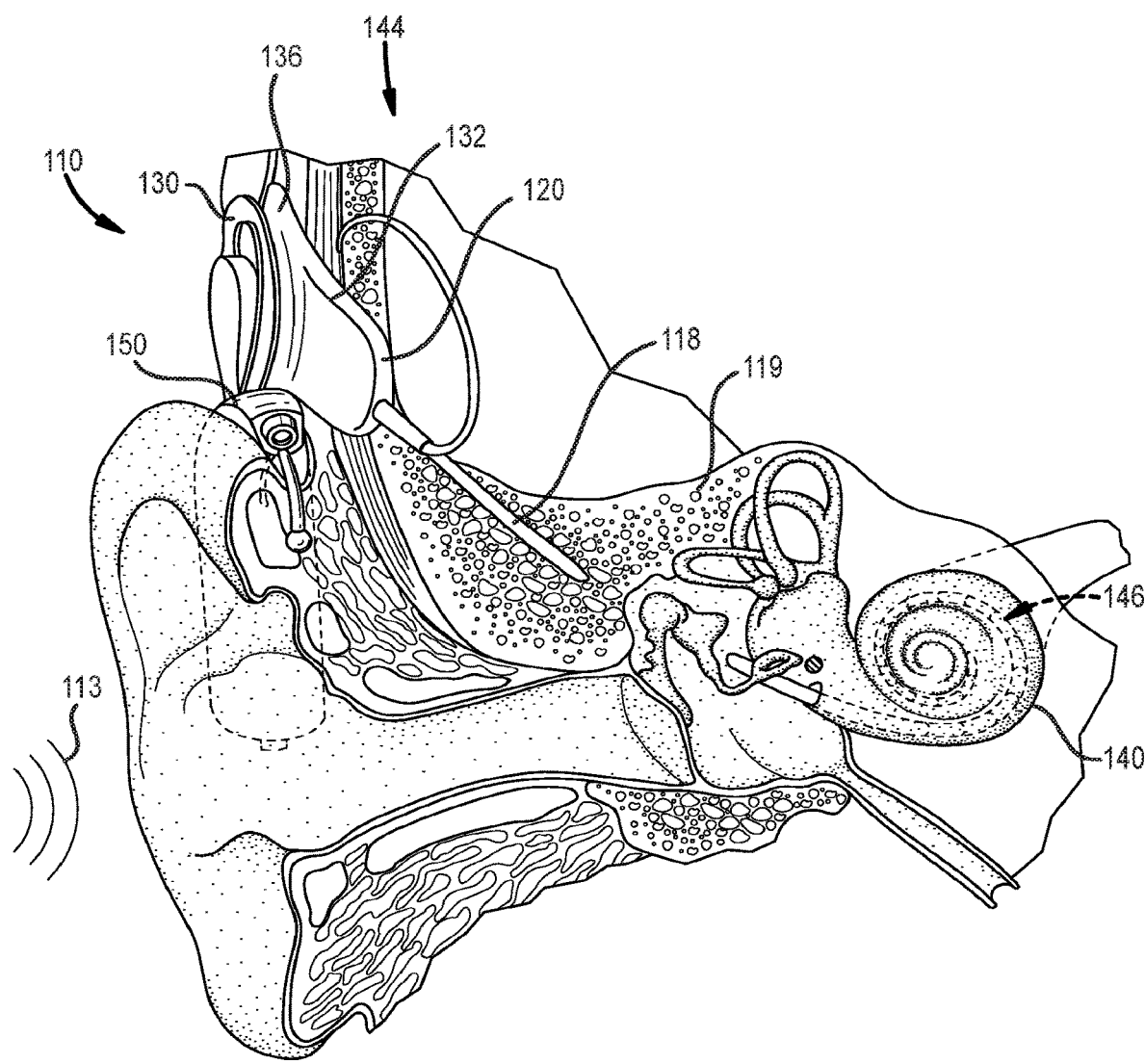
FIG. 1 illustrates an example cochlear implant system that includes an implantable component that can benefit from the use of a monolithic medical device component in accordance with certain embodiments of the invention.

The disclosed monolithic medical device components can be implemented in any of a variety of systems in accordance with embodiments of the invention. For example, in many embodiments, monolithic medical device components are implemented within a conventional cochlear implant system. FIG. 1 depicts a conventional cochlear implant system that can benefit from the integration of monolithic medical device components in accordance with certain embodiments of the invention. In particular, FIG. 1 illustrates an example cochlear implant system 110 that includes an implantable component 144 typically having an internal receiver/transceiver unit 132, a stimulator unit 120, and an elongate lead 118. The internal receiver/transceiver unit 132 permits the cochlear implant system 110 to receive and/or transmit signals to an external device 150. The external device 150 can be a button sound processor worn on the head that includes a receiver/transceiver coil 130 and sound processing components. Alternatively, the external device 150 can be just a transmitter/transceiver coil in communication with a behind-the-ear device that includes the sound processing components and microphone. The implantable component 144 includes an internal coil 136, and preferably, a magnet (not shown) fixed relative to the internal coil 136. The magnet can be embedded in a pliable silicone or other biocompatible encapsulant, along with the internal coil 136. Signals sent generally correspond to external sound 113. The internal receiver/transceiver unit 132 and the stimulator unit 120 are hermetically sealed within a biocompatible housing, sometimes collectively referred to as a stimulator/receiver unit. Included magnets (not shown) can facilitate the operational alignment of the external and internal coils, enabling the internal coil 136 to receive power and stimulation data from the external coil 130. The external coil 130 is contained within an external portion. The elongate lead 118 has a proximal end connected to the stimulator unit 120, and a distal end 146 implanted in a cochlea 140 of the recipient.

The elongate lead 118 extends from stimulator unit 120 to the cochlea 140 through a mastoid bone 119 of the recipient.

In certain examples, the external coil 130 transmits electrical signals (e.g., power and stimulation data) to the internal coil 136 via a radio frequency (RF) link. The internal coil 136 is typically a wire antenna coil having of multiple turns of electrically insulated single-strand or multi-strand platinum or gold wire. The electrical insulation of the internal coil 136 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Figure 2A:
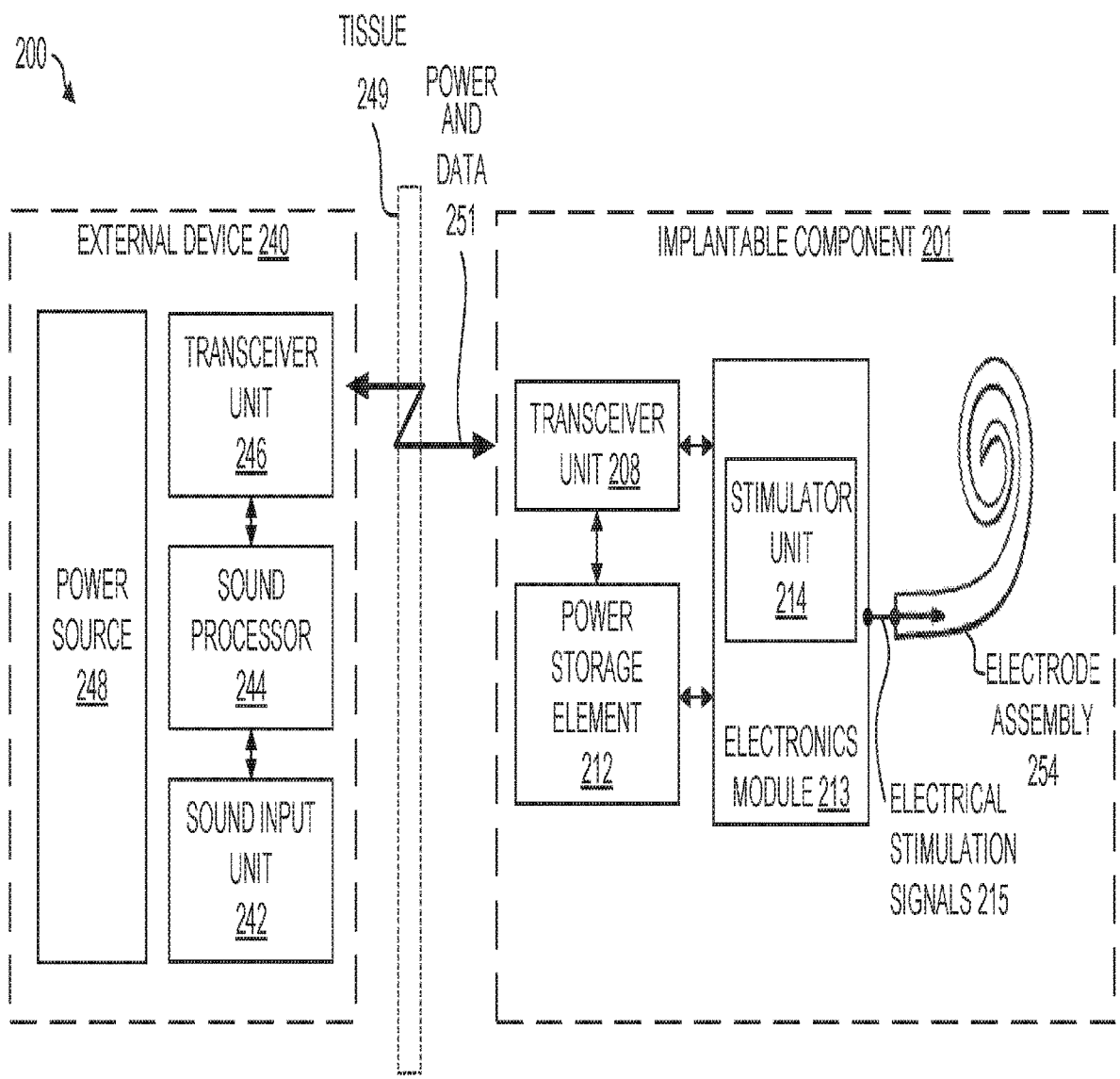
FIG. 2A is a functional block diagram of an example cochlear implant that can benefit from the use of a monolithic medical device component in accordance with certain embodiments of the invention.

FIG. 2A is a functional block diagram of a cochlear implant 200 that can benefit from the use of a monolithic medical device component in accordance with certain embodiments described herein. The cochlear implant 200 includes an implantable component 201 (e.g., implantable component 144 of FIG. 1) configured to be implanted beneath a recipient's skin or other tissue 249, and an external device 240 (e.g., the external device 150 of FIG. 1).

Implantable component 201 can include a transceiver unit 208, a power storage element 212, electronics module 213, and an electrode assembly 254 (which may include an array of electrode contacts disposed on lead 118 of FIG. 1). The transceiver unit 208 is configured to transcutaneously receive power and/or data from external device 240. As used herein, transceiver unit 208 refers to any collection of one or more implanted components which form part of a transcutaneous energy transfer system. Further, transceiver unit 208 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data from the external device 240 to the implantable component 201.

Power storage element 212 is configured to store power. The power storage element 212 can include, for example, one or more rechargeable batteries. As described below, power can be received from an external device, such as the external device 240, and stored in the power storage element 212. The power can then be distributed to the other components of the implantable component 201 as needed for operation.

As shown, electronics module 213 includes a stimulator unit 214 (e.g., which may correspond to stimulator 120 of FIG. 1). Electronics module 213 can also include one or more other components used to generate or control delivery of electrical stimulation signals 215 to the recipient. As described above with respect to FIG. 1, a lead (e.g., elongate lead 118 of FIG. 1) may be inserted into the recipient's cochlea. The lead can include an electrode assembly 254 configured to deliver electrical stimulation signals 215 generated by the stimulator unit 214 to the cochlea.

In the embodiment depicted in FIG. 2A, the external device 240 includes a sound input unit 242, a sound processor 244, a transceiver unit 246, and a power source 248. The sound input unit 242 is a unit configured to receive sound input. The sound input unit 242 can be configured as a microphone, an electrical input for an FM hearing system, and/or another component for receiving sound input. The sound processor 244 is a processor configured to convert sound signals received from sound input unit 242 into data signals. The transceiver unit 246 is configured to send power and data 251. The transceiver unit can also be configured to receive power or data. The data signals from the sound processor 244 can be transmitted, using the transceiver unit 246, to the implantable component 201 for use in providing stimulation.

As should be appreciated, while a particular cochlear implant that can benefit from utilizing the disclosed monolithic medical device components has been illustrated and discussed above, the disclosed monolithic medical device components can be integrated in any of a variety of implantable medical devices in accordance with many embodiments of the invention. The above discussion is not meant to suggest that the disclosed monolithic medical device components are only suitable for implementation within systems akin to that illustrated in and described with respect to FIGS. 1 and 2A. In general, additional configurations can be used to practice the methods and systems herein and/or some aspects described can be excluded without departing from the methods and systems disclosed herein.

Figure 2B:
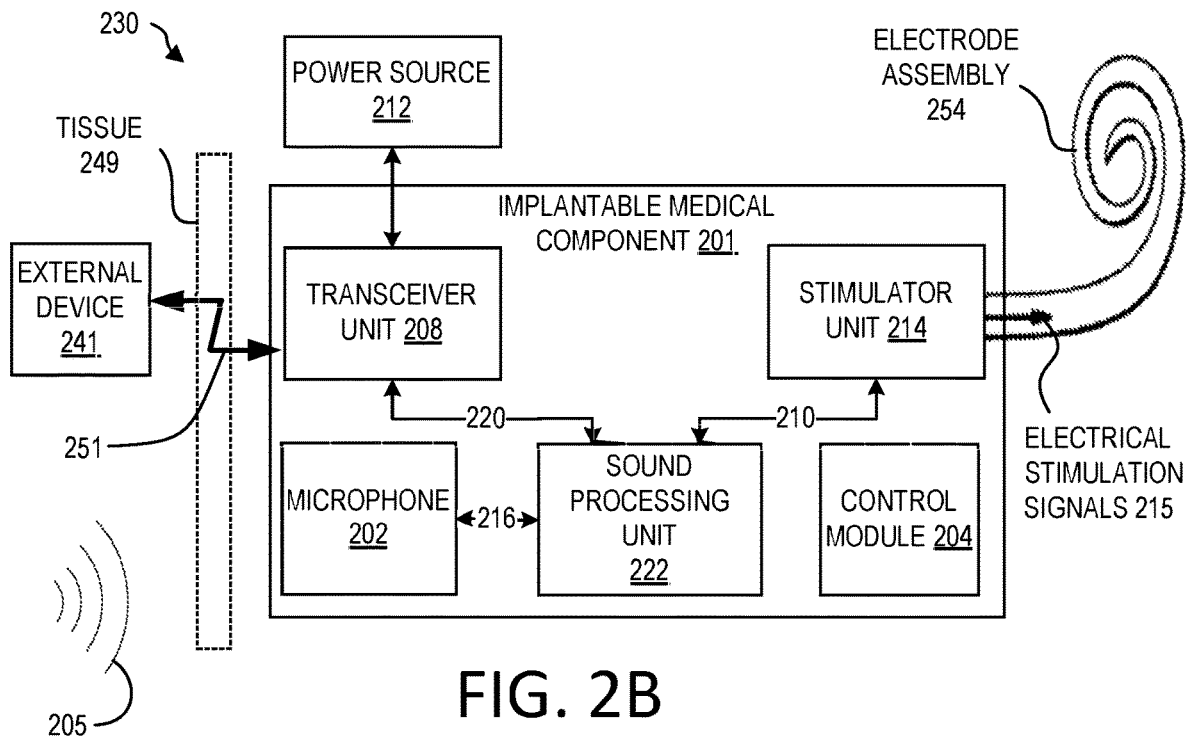
FIG. 2B is a functional block diagram of an exemplary totally-implantable cochlear implant system that can benefit from the use of a monolithic medical device component in accordance with certain embodiments of the invention.

For example, in many embodiments, monolithic medical device components disclosed can be implanted in a totally implantable cochlear implant. FIG. 2B is a functional block diagram illustrating an example cochlear implant system 230 that is totally implantable, which can benefit from the inclusion of monolithic medical device components described herein; the depicted cochlear implant system 230 is totally implantable insofar as all components of cochlear implant system 230 are configured to be implanted under skin or tissue 249 of the recipient. Because all components of the cochlear implant system 230 are implantable, the cochlear implant system 230 can operate, for at least a finite period of time, without the need of an external device. An external device 241 can be used to charge the internal battery, to supplement the performance of the implanted microphone/system, or for when the internal battery no longer functions. The external device 241 can be a dedicated charger or a conventional cochlear implant sound processor (e.g. a 'behind-the-ear' sound processor or a 'button sound processor').

The cochlear implant system 230 includes a main implantable component 201 having a hermetically sealed, biocompatible housing. Disposed in the main implantable component 201 is a microphone 202 configured to sense a sound signal 205 and provide an output. The microphone 202 can include one or more components to pre-process the microphone output. As an alternative, the microphone and other aspects of the system can be included in an upgrade or tethered module as opposed to in a unitary body as shown in FIG. 2B.

An electrical signal 216 representing a sound signal 205 detected by microphone 202 is provided from the microphone 202 to the sound processing unit 222. The sound processing unit 222 implements one or more speech processing and/or coding strategies to convert the pre-processed microphone output into data signals 210 for use by the stimulator unit 214. The stimulator unit 214 uses data signals 210 to generate electrical stimulation signals 215 for delivery to the cochlea of the recipient. In the example of FIG. 2B, the cochlear implant system 230 includes an electrode assembly 254 for delivering stimulation signal 215 to the cochlea.

The main implantable component 201 further includes a control module 204. The control module 204 includes various components for controlling the operation of the cochlear implant system 230, or for controlling specific components of the cochlear implant system 230. For example, the control module 204 can control the delivery of power from a power storage element 212 of the cochlear implant system 230 to other components of the system 230. For ease of illustration, the main implantable component 201 and the power storage element 212 are shown as separate. However, the power storage element 212 can alternatively be integrated into a hermetically sealed housing or part of a separate module coupled to the component 201. The hermetically sealed housing can be constructed from a biocompatible material, such as titanium.

As noted above, the cochlear implant system 230 further includes a receiver or transceiver unit that permits the cochlear implant system 230 to receive and/or transmit signals from/to an external device 241. For ease of illustration, the cochlear implant system 230 is shown having a transceiver unit 208 in the main implantable component 201. In alternative arrangements, the cochlear implant system 230 includes a receiver or transceiver unit which is implanted elsewhere in the recipient outside of the main implantable component 201.

As noted, the transceiver unit 208 receives power and/or data from the external device 241. The external device 241 can include a power source (not shown) disposed in a Behind-The-Ear (BTE) unit. The external device 241 also includes components of a transcutaneous energy transfer link formed with the transceiver unit 208 to transfer the power and/or data to the cochlear implant system 230.

The external device shown in FIG. 2B is merely illustrative, and other external devices can be alternatively used. Further, as should be appreciated, the various aspects (e.g., devices, components, etc.) described with respect to FIG. 2B are not intended to limit the systems and methods to the particular aspects described. Accordingly, additional configurations can be used to practice the methods and systems herein and/or some aspects described can be excluded without departing from the methods and systems disclosed herein. To be clear, the monolithic medical device components described below can be integrated in any of a variety of implantable medical devices in accordance with embodiments of the invention.

Importantly, while FIG. 2B illustrates a block diagram of a totally implantable cochlear implant system, it should be noted that the system can be implemented using any suitable architecture. For example, in many embodiments, the implemented architecture can be characterized by a portion having a telemetry coil, a portion having certain electronics, and a portion having an electrode assembly. Thus for instance, FIG. 2C illustrates a cochlear implant system characterized by a coil portion, an electronics module portion, and an electrode assembly portion, where the electrode module portion includes a transceiver unit, a sound processor, a stimulator unit, and a power storage element.

Figure 2C:
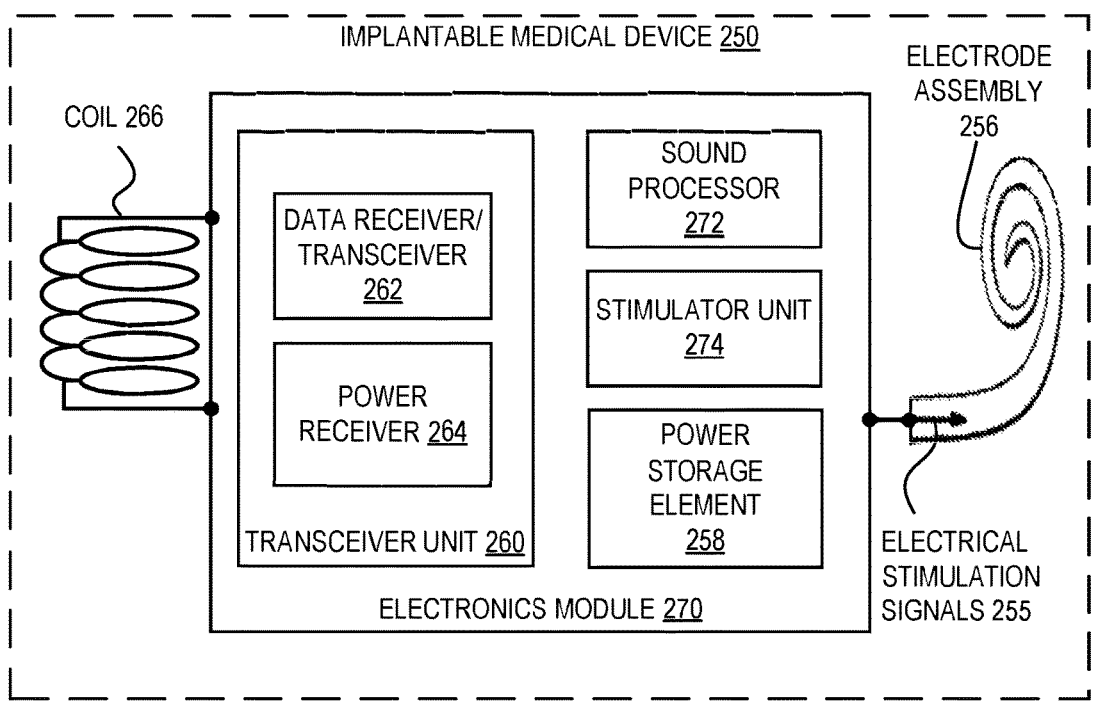
FIG. 2C is a functional block diagram of an example implantable medical device that can benefit from the use of a monolithic medical device component in accordance with certain embodiments of the invention.

In particular, FIG. 2C illustrates an implantable medical device 250 configured to be implanted beneath a recipient's skin or other tissue. The implantable medical device 250 can include an electrode assembly 256, a coil 266, and an electronics module 270. The components of the implantable medical device 250 can include one or more characteristics and/or components of devices discussed elsewhere herein, including FIGS. 1, 2A, and 2B.

As illustrated, the electrode assembly 256 is disposed on an elongate lead (e.g., elongate lead 118 of FIG. 1) and is configured to deliver electrical stimulation signals 255 to target anatomy (e.g., a cochlea as previously described) using an array of electrode contacts. In some examples, the electrode assembly 256 can include sensing electrodes or other components for sensing characteristics of target anatomy.

The electronics module 270 can include components such as a power storage element 258, a transceiver unit 260, a sound processor 272, and a stimulator unit 274).

Power storage element 258 is configured to store power, such as power received by transceiver unit 260 (e.g., from an external power source), and to distribute power, as needed, to the elements of implantable medical device 250.

The transceiver unit 260 can include a data receiver/transceiver 262 and a power receiver 264. These components 262, 264 can use the coil 266 to transmit or receive data and power from other components, such as from an external device (not shown). This can be through a transcutaneous communication link over which data and power is transferred from an external transceiver unit to the implantable medical component 250. The coil 266 can include one or more antenna coils. The transcutaneous communication link can include a magnetic induction link. The transcutaneous communication link established by the transceiver unit 260 can use time interleaving of power and data on a single radio frequency (RF) channel or band to transmit the power and data to the implantable medical device 250. In an example, the data modulates the RF carrier or signal containing power.

The sound processor 272 is a processor configured to convert sound signals received from a sound input unit (not shown) into data signals. The sound input unit can be located within the implantable medical device 250 (e.g., as in a totally-implanted cochlear implant) and/or within an external device (not shown).

The stimulator unit 274 can use data signals to generate electrical stimulation signals 255 for delivery using the electrode assembly 256. The electronics module 270 can also include one or more other components used to generate or control delivery of electrical stimulation signals 255 to the recipient. The electrode assembly 256 can be inserted into the recipient's cochlea and deliver electrical stimulation signals 255 generated by stimulator unit 274 to the cochlea.

Again, it should be clear that while a certain architecture for a totally implantable cochlear implant has been discussed above, the monolithic medical device components discussed herein can be integrated into cochlear implants adopting any of a variety of architectural configurations in accordance with embodiments of the invention. For example, in many embodiments, the power storage element and/or the sound processor are separate from the electronics module. Indeed, the monolithic medical device components disclosed herein can be integrated into any of a variety of implantable medical devices in accordance with embodiments of the invention.

Figure 3:
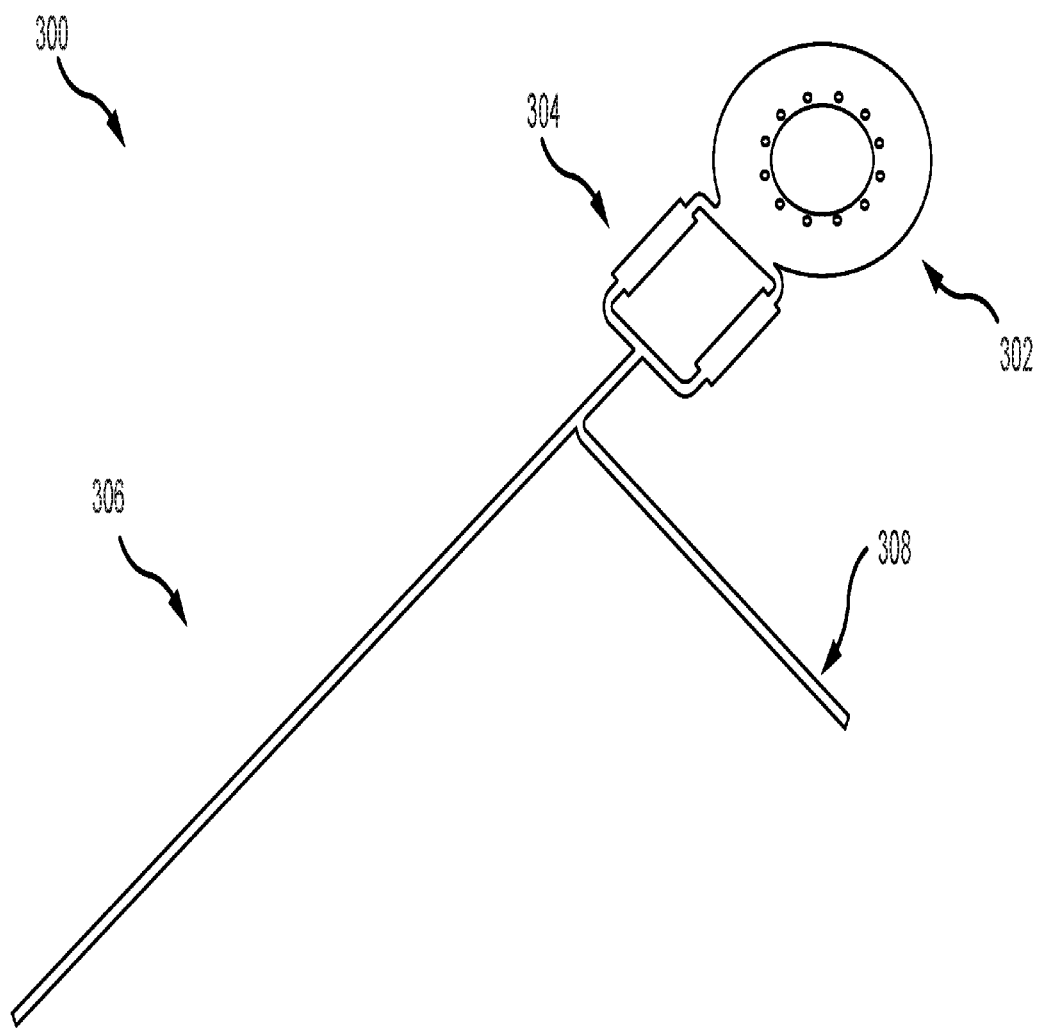
FIG. 3 illustrates an example monolithic implantable medical component having multiple regions in accordance with certain embodiments of the invention.

FIG. 3 illustrates an example monolithic implantable medical component 300 having two or more regions that can be implanted in a medical device (such as those described above) in accordance with many embodiments of the invention. The implantable medical component 300 can be a monolithic component by having a single-body design in which the component's regions or parts are integral. For example, the regions are portions of a same whole, rather than separately supplied components connected together via one or more connection interfaces (e.g., plugs or other connectors configured to connect two or more discrete components). The regions of the monolithic implantable medical component can be formed on a same substrate. The regions of the monolithic implantable medical component 300 need not all be electrically connected to each other but, in many instances, two or more portions or components thereof can be electrically connected.

In the illustrated example, the monolithic implantable medical component 300 includes a telemetry coil region 302, an electrical interface region 304, a first anatomy interface region 306, and a second anatomy interface region 308. The monolithic implantable medical component 300 can include different or additional components, such as one or more circuits or electronics integrated into the component 300 for performing one or more functions including but not limited to signal processing, energy storage, treatment, or other functions. In some embodiments, the electric interface region can include integrated circuit traces, and can thereby function as a printed circuit board.

The telemetry coil region 302 is a portion of the monolithic implantable medical component 300 that includes an inductance coil adapted to receive a signal. The signal can include data or power signals from a coil of an external device. Although shown as a single coil, the implantable component can include two or more telemetry coils or one or more other components for receiving data or power. In some examples, the telemetry coil region 302 is configured to transmit data and/or power signals.

The electrical interface region 304 is a portion of the monolithic implantable medical component 300 adapted to electrically connect the implantable component to an electronics module (e.g., electronics module 270 depicted above) or other components. The electronics module in one example, can include a processing unit and one or more functional components used to generate or control delivery of electrical stimulation signals or monitor activity using a sensor. For example, the electronics module can generate and control delivery of electrical stimulation signals to an electrode assembly that interfaces with anatomy of a recipient (e.g., an inserted into the recipient's cochlea and interfaces with the cochlea by providing stimulation using one or more electrodes). In another example, the electronics module can receive signals from a sensor region that interfaces with anatomy of a recipient.

In some examples, an electrical pathway between the electronics module and the electrical interface region 304 can be made through one or more components of the electrical interface region 304 that are electrically connectable to the electronics module, such as one or more pads, pins, or other conductive regions. In some examples, the pathway can be made through a feedthrough associated with the electronics module. In other examples, the electronics module is disposed in direct contact with the electrical interface region 304 to form an electrical pathway.

The electrical interface region 304 can provide the electrical pathway between the electronics module and portions of the implantable medical component 300, such as the telemetry coil region 302, the first anatomy interface region 306 and/or the second anatomy interface region 308. For example, one or more electrical pathways (e.g., a trace or wire) can connect one or more of the portions of the implantable medical component 300 to the electrical interface region 304 or to each other.

In an example, there can be one or more electrical pathways between the telemetry coil region 302 and the electrical interface region 304. An electronics module can be electrically connected to the telemetry coil region 302 via the electrical interface region 304. The electronics module can have an output module configured to take an action based on at least in part on a signal received at the telemetry coil region 302. For instance, there can also be an electrical pathway between the electrical interface region 304 and the first or second anatomy interface regions 306, 308. Through these pathways, the electronics module can emit an output stimulation through the first or second anatomy interface regions 306, 308 based at least in part on a signal received at the telemetry coil region 302. In another example, the electronics module can include a processor configured to take an action based on input received from a sensor or telemetry coil component of the monolithic implantable medical component 300.

The first anatomy interface region 306 is a portion of the monolithic implantable medical component 300 that interfaces with a target anatomy of a patient in which the monolithic implantable medical component 300 is implanted. In an example, the first anatomy interface region 306 can include one or more electrodes that deliver electrical stimulation to a target region of the patient's anatomy (e.g., the cochlea 140). In some embodiments, the anatomy interface region can include platinum contact pads to facilitate the delivery of electrical stimulation; platinum can have favorable engineering characteristics in a number of respects. Note that platinum can be implemented using known thin film deposition techniques. In several embodiments, the first anatomy interface region 306 can include one or more return electrodes. In still another example, the first anatomy interface region 306 can include one or more sensors for sensing a property or characteristic of the target anatomy. The first anatomy interface region 306 can be directly or indirectly electrically connected to one or more of the other components of the implantable medical component 300 or another component (e.g., an electronics module connected to the electrical interface region 304 or an external device). The first anatomy interface region 306 can take an action based in part on the direct or indirect pathway. For example, the first anatomy interface region 306 can provide sensed data over the electrical pathway. As another example, the first anatomy interface region 306 can provide treatment using the electrical pathway (e.g., delivering stimulation to a target anatomy).

The optional second anatomy interface region 308 is also a portion of the monolithic implantable medical component 300 that interfaces with a target anatomy of a patient in which the monolithic implantable medical component 300 is implanted. It can have one or more properties described in relation to the first anatomy interface region 306. In a particular example, the first anatomy interface region 306 can include an array of electrodes for providing stimulation while the second anatomy interface region 308 functions as a return electrode portion.

While a specific implantable monolithic medical device component has been described above in association with FIG. 3, embodiments of the invention are not constrained to the specific component illustrated in FIG. 3. Implantable monolithic medical device components can be implemented in any of a variety of ways in accordance with embodiments of the invention. For example, as already alluded to above, in many embodiments, implantable monolithic medical device components do not include a second anatomy interface region. In some embodiments, a monolithic medical device component includes an anatomy interface region that is configured to act as a sensor. In several embodiments, the sensor can be a microphone. Accordingly, in many embodiments, monolithic medical device components can be used in the implementation of implantable microphones. Note also that the various regions can adopt any of a variety of geometries, and can be spatially oriented relative to one another in any of a variety of suitable ways in accordance with many embodiments of the invention. In several embodiments, the electrical interface region includes integrated electronics, such as integrated circuits, capacitors, resistors, and the like.

Figure 4:
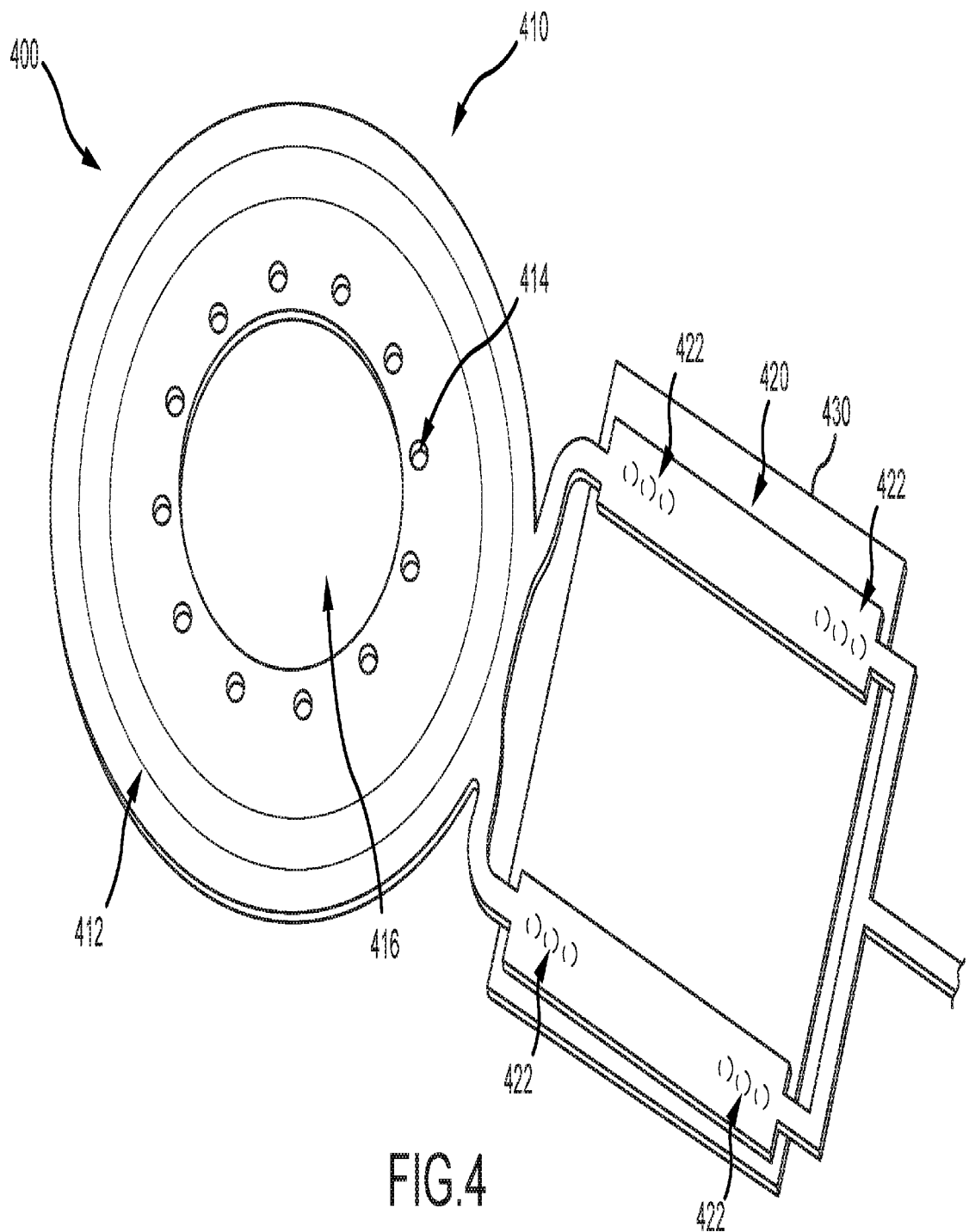
FIG. 4 illustrates an example portion of a monolithic implantable medical component including a telemetry coil region and an electrical interface region in accordance with certain embodiments of the invention.

FIG. 4 illustrates an example portion of a monolithic implantable medical component 400 (e.g. as described in relation to monolithic implantable medical component 300 of FIG. 3) including a telemetry coil region 410, an electrical interface region 420, and an electronics module 430 connected to the electrical interface region 420. The telemetry coil region 410 can include one or more components or properties of the telemetry coil region 302 shown and described in relation to FIG. 3. The telemetry coil region 410 can include a telemetry coil 412 disposed between layers of substrate or other material. The layers of substrate or other material can define one or more through holes 414 and an aperture 416. The telemetry coil 412 is a region adapted to receive a signal (e.g., a power or data signal), such as via induction. The telemetry coil 412 can include one or more antenna coils. The one or more antenna coils can include one or more turns of electrically conductive material. For example, there can be one or more turns of electrically conductive material deposited on the substrate in one or more layers. In another example, there can be multiple turns of electrically insulated single-strand or multi-strand wire (e.g., platinum or gold wire). The antenna coils can be formed on one or more layers of substrate.

The through holes 414 are regions defined by missing material in the telemetry coil region 410. For example, the telemetry coil 412 can be disposed between layers of substrate or other material and the through holes 414 can be a region of missing material extending entirely through the substrate or other material. The through holes 414 can facilitate anchoring the telemetry coil region 410. For example, the through holes 414 can anchor the telemetry coil region to a biocompatible housing of a medical device in which the telemetry coil region 410 is disposed. For instance, the telemetry coil region 410 can be disposed within a silicone housing, and the through holes 414 can be regions in which material, such as a silicone rivet, extends to facilitate anchoring the telemetry coil 412 in the housing. The silicone rivet can resist movement of the telemetry coil region 410 in the housing. The aperture 416 is a region defined by missing material (e.g., material in which the coil 412 is disposed) in the telemetry coil region 410 sized and shaped to accommodate a magnet. For example, in some embodiments, the telemetry coil region 410 is disposed around a magnet placed inside the aperture 416.

The electrical interface region 420 can include one or more electrical connections 422. The electrical connections 422 are electrically conductive regions that facilitate connection of the monolithic implantable medical component 400 to the electronics module 430. The electrical connections 422 can include conductive pads, conductive pins, mounting through holes, or other electrically conductive components. The electronics module 430 can include portions compatible with the electrical connections 422 for establishing a connection with one or more components or regions of the monolithic implantable medical component 400. For example, there can be one or more electrical connections 422 associated with (e.g., electrically connected to) the coil 412. These electrical connections associated with the coil 412 can allow for signals (e.g., power or data signals) received at the coil 412 to be provided over the electrical connection 422 to a component (e.g., the electronics module 430) connected thereto. Similarly, a signal can be received over the electrical connection 422 from a component connected thereto, and the signal can be transmitted (e.g., over an electrical pathway such as a trace) to another portion of the implantable monolithic component 400 (e.g., an anatomy interface region as shown and described in relation to FIG. 3).

The number and configuration of the electrical connections 422 can vary depending on the components and regions of the monolithic implantable medical component 400. For example, in some embodiments the medical component 400 includes a plurality of electrodes (e.g., the first or second anatomy interface regions 306, 308 described in FIG. 3 can each include one or more electrodes). There can be at least one electrical connection 422 corresponding to each of the electrodes. The electrical connections 422 can then facilitate delivery of electrical stimulation or other therapy via the corresponding electrodes as controlled by the electronics module 430. In another example, the medical component 400 includes a plurality of sensors (e.g., sensors disposed on the first or second anatomy interface regions 306, 308 described in FIG. 3) which include one or more corresponding electrical connections 422.

Again, while a particular telemetry coil region and electronics interface region has been illustrated in and discussed with respect to FIG. 4, it should be clear that these regions can be implemented in any of a variety of ways in accordance with embodiments of the invention. For example, in some embodiments, the telemetry coil region does not include apertures or through holes.

Figure 5:
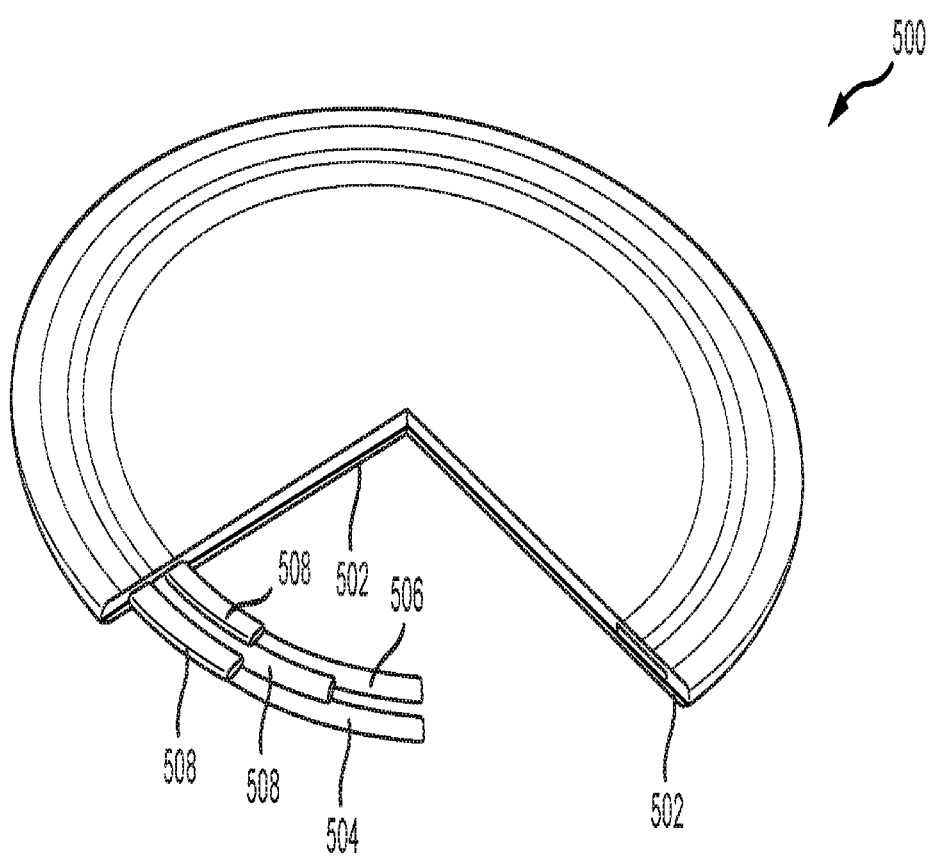
FIG. 5 illustrates an example cutaway view of a coil that can be implemented in accordance with certain embodiments of the invention.

FIG. 5 illustrates an example cutaway view of a coil 500. In the illustrated coil 500 there is a substrate 502 on which a first conductive material turn 504 and a second conductive material turn 506 are disposed. These conductive material turns 504, 506 can be connected to each other as part of the same coil 500, but are generally separated from each other and from other components by insulating regions 508. Although illustrated as having two turns, the coil 500 can have a greater or fewer number of turns. In some examples, the coil 500 can include a plurality of layers of turns, which can allow for more turns of the coil 500 in a smaller space. In the illustrated embodiment, the region near the coil 500 does not have one or more through holes or an aperture (e.g., through holes 414 or aperture 416 of FIG. 4) defined in the substrate 502 or other material. To be clear, any suitable telemetry coil can be incorporated in accordance with embodiments of the invention.

Figure 6:
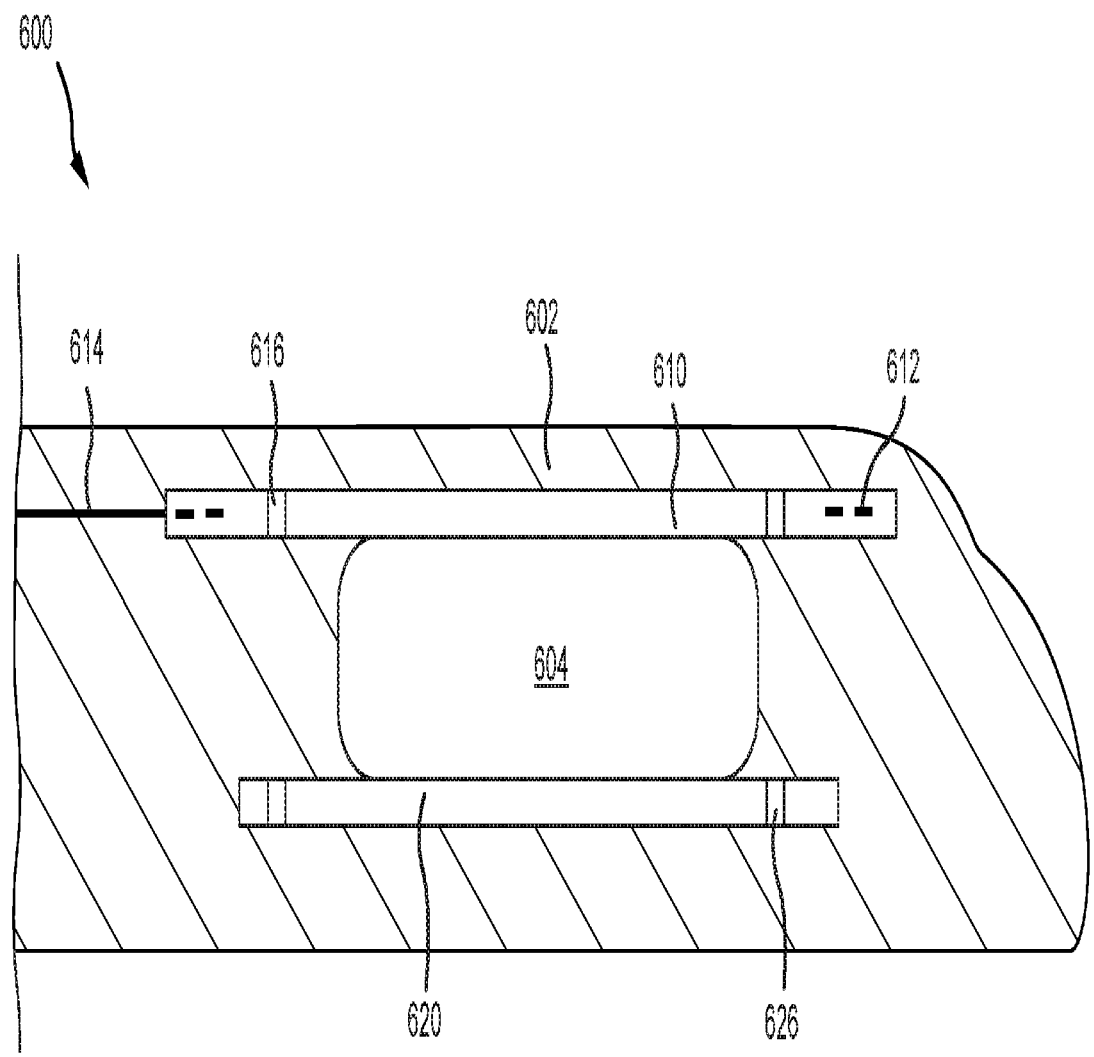
FIG. 6 illustrates an example portion of an implantable medical device including a coil that can be implemented in accordance with certain embodiments of the invention.

FIG. 6 illustrates an example implantable medical device 600. The example implantable medical device 600 includes a body material 602. Disposed within the body material 602 are a magnet 604, a first plate 610, and a second plate 620. The body material 602 can be a biocompatible elastomeric material suitable for housing an implantable medical device, such as medical grade silicone.

In some embodiments, the magnetic field of the magnet 604 can interact with a magnetic field of an external magnet. For example, the magnet 604 can facilitate alignment of an external medical device with the implantable medical device 600. In addition or instead, the magnet 604 can modify an electric or magnetic field associated with a coil or a signal.

The plate 610 is a component or region of the medical device 600 that resists rotation or movement of the magnet 604, such as rotation of the magnet 604 when the magnet 604 is subjected to an externally-generated magnetic field (e.g., from an MRI procedure) that imparts a torque on the magnet 604. When resisting rotation, the medical device 600 or plate 610 can permit a modicum of rotation of the magnet 604. In at least some embodiments, some initial rotation is required so as to push the plate 610 to create force that resists further rotation. This resistance can be facilitated by an interaction between the plate 610 and the body material 602 of the implantable medical device 600. In some examples the plate 610 is a disc, but the plate 610 can have other shapes or configurations. In some examples, the plate 610 can have a higher rigidity than the body material 602. For instance, the plate 610 can be about 0.5, 1, 1.5, 2, or 3 or more orders of magnitude more rigid than the body. In some embodiments, the plate 610 can be constructed from polytetrafluoroethylene (PTFE), polyphenylsulfone (PPSU), ceramic, or other materials or combinations thereof. The body material 602 can be molded about the plate 610 such that the plate 610 is not removable from the body material of the implantable medical device 600 without purposefully destroying a portion of the body of the medical device 600.

The plate 610 can further include a telemetry coil 612. The telemetry coil 612 can be a telemetry coil portion of a monolithic implantable medical component 614 (e.g., having one or more properties or characteristics of the monolithic implantable medical component described herein). The telemetry coil 612 can be disposed in relation to the plate 610, such as on top of, beneath, or within the plate 610. In some examples, the coil 612 can be directly attached to the plate 610 or held in relation to the plate (e.g., both are disposed in the body material 602 such that the body material holds them in relation to each other, but they are not directly attached to one another). The plate 610 can have one or more through holes 616 to facilitate anchoring the plate 610 to the body material 602 or the coil 612. The through holes 616 can align with one or more through holes of the coil 612. In effect, the telemetry coil region of a monolithic implantable medical device component, such has those descried with respect to FIGS. 3-5 can be configured to act as a plate in accordance with many embodiments of the invention.

The second plate 620 can be a component or region of the medical device 600 that resists rotation or movement of the magnet 604. The second plate 620 can have one or more properties described in relation to the first plate 610. In some examples, the coil 612 is embedded in the second plate 620 in addition to or instead of the first plate 610. In some examples, the coil 612 is embedded in the first plate 610 and an additional coil separate from the first coil is embedded in the second plate 620. In some examples, the second plate 620 can include additional circuit traces. The second plate 620 can cooperate with the first plate 610 to resist rotation or movement of the magnet 604. The second plate can also include through holes 626. In some examples, a rivet or material can extend through the through holes 616 and the through holes 626.

The magnet 604 can be disposed between the first plate 610 and the second plate 620. In some examples, the first plate 610 is arranged in the medical device 600 such that the first plate 610 is located closer to an exterior of the patient (e.g. closer to the skin) then the second plate 620. Disposing the coil 612 proximate the first plate 610 rather than the second plate 620 (e.g., closer to the skin) can facilitate better communication between the coil 612 and an external coil of an external medical device by improving coil efficiency.

Figure 7:
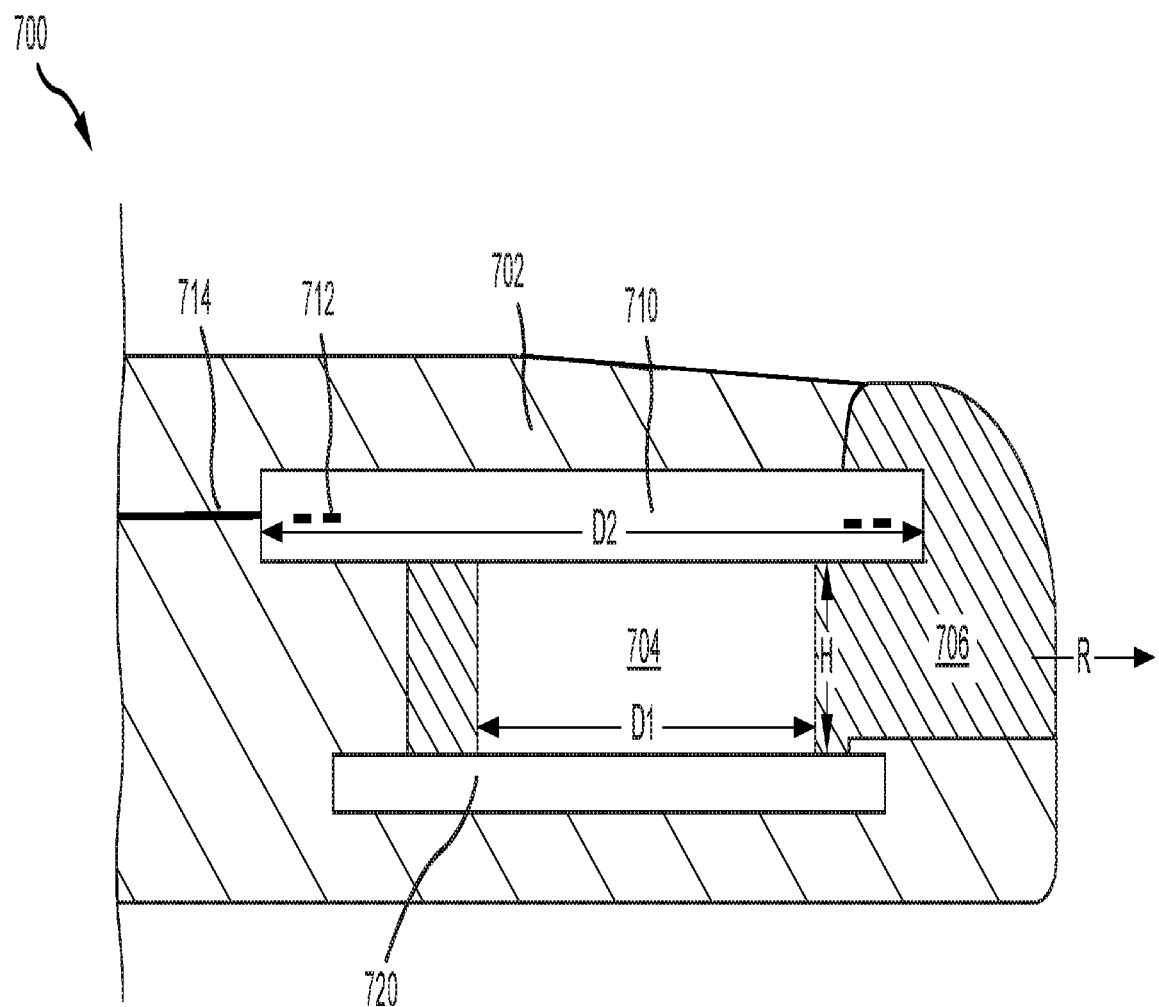
FIG. 7 illustrates an example portion of an implantable medical device including a coil that can be implemented in accordance with certain embodiments of the invention.

FIG. 7 illustrates an example implantable medical device 700. The medical device 700 can include one or more components or properties described in relation to the implantable medical device 600. As such, not all elements depicted in FIG. 7 are necessarily described further. As illustrated, the medical device 700 includes a body material 702 and a magnet 704 disposed within a cassette 706. The medical device 700 further includes a first plate 710 and a second plate 720. A coil 712 can be disposed in relation to the first plate 710. For example, the coil 712 can be integrated into the first plate 710. The coil 712 can be part of a monolithic implantable medical component 714.

The cassette 706 can be a component in which the magnet 704 is disposed and facilitates removal of the magnet 704 from the implantable medical device 700. For example, the cassette 706 can house or otherwise connect to the magnet 704 such that movement of the cassette 706 moves the magnet 704. The cassette 706 can be disposed in a sliding relationship with the implantable medical device 700 such that the magnet 704 can be removed by sliding the cassette 706 out of the implantable medical device 700 without destroying or damaging the body of the implantable medical device 700.

In the illustrated embodiment, because the coil 712 is not disposed around the magnet 704, the magnet 704 can be removed from the medical device 700 in a removal direction R substantially perpendicular to the height H of the magnet 704 (e.g., substantially parallel to the diameter D1 of the magnet 704 where the magnet 704 is cylindrical) without necessarily disturbing the coil 712. In another example, the magnet 704 can be slid out from the medical device 700 in a removal direction R substantially parallel to an outer diameter D2 of the coil 712. By contrast, if the coil 712 were disposed around the magnet 704 (e.g., where the magnet is disposed within an aperture of a coil region) the magnet 704 would be removed by moving the magnet 704 in a direction perpendicular to the outer diameter D2 of the coil 712 (e.g., because the coil 712 would surround the magnet 704 and block its movement parallel to the diameter D2 of the coil 712) rather than by removing it in a direction parallel to the coil 712. In some embodiments, the cassette 706 can be configured to provide a smooth surface to discourage biofilms. For example, as illustrated, the cassette 706 can wrap around a front of the coil 712 to protect the lip and create a smooth surface. This can inhibit the development of biofilms.

Figure 8:
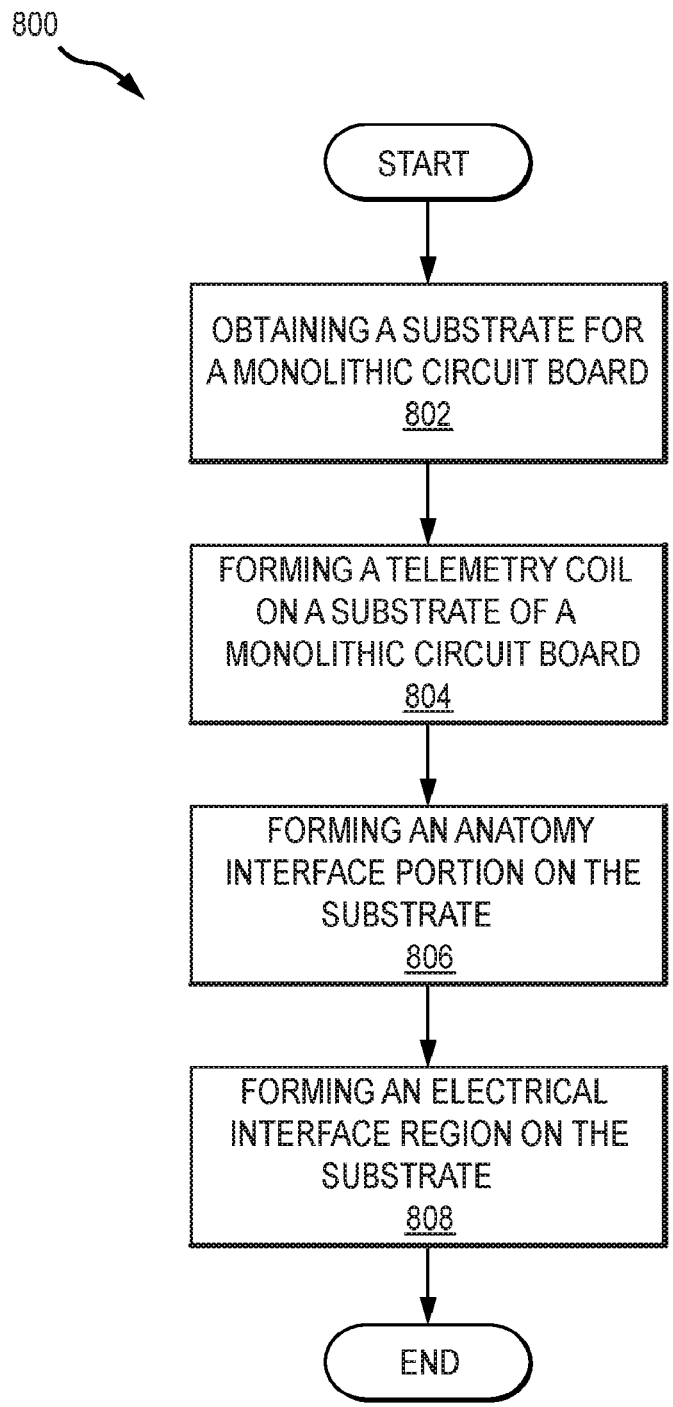
FIG. 8 illustrates an example process for manufacturing an implantable medical component in accordance with certain embodiments of the invention.

FIG. 8 illustrates an example process 800 for manufacturing an implantable medical component (e.g., implantable medical component 300). The process 800 can begin with step 802, which involves obtaining a substrate for a monolithic circuit board. Step 802 includes acquiring a substrate with which the monolithic circuit board will be formed. The substrate can be made from a material suitable for forming a flexible printed circuit board. The substrate can be formed from a flexible plastic, such as a liquid crystal polymer, polyimide, polytetrafluoroethylene, or polyether ether ketone, among others. The substrate can be a thin, flexible sheet of the material. The substrate can be preconfigured by having a particular shape or other features. In some embodiments, the obtained substrate can already have one or more electrical components or other features formed on it. The substrate can be sized and shaped to accommodate the one or more features that will be formed on it (e.g. a telemetry coil portion, an electrical interface portion, a first anatomy interface portion, and a second anatomy interface portion) without needing to couple separate parts to the substrate.

In some embodiments, the substrate can have different qualities in different portions. For example, a first region of the substrate can have a first property (e.g., a particular flexibility because the first region the substrate is formed from a particular material) and a second region of the substrate can have a second property (e.g., a different flexibility because the second region of the substrate is formed from a different material). In an example, the substrate can be treated (e.g., thermally, chemically, etc.) differently in different regions to create different portions with different material properties.

Step 804, step 806, and step 808 involve forming various regions or components on the substrate. The steps 804, 806, and 808 can involve disposing electrically conductive materials on the substrate to form a particular component or region. This can include the use of photolithography, disposing etched conductive sheets on the substrate, laying a conductive trace, or another process for forming a circuit or a portion thereof on the substrate. These steps can include disposing the electrically conductive material on or across multiple layers of substrate. For example, layers of conductive and/or insulative materials can be sequentially deposited to develop a desired structure. The multiple layers can be connected or independent.

Step 804 involves forming a telemetry coil on a substrate of a monolithic circuit board. This step 804 can involve disposing electrically conductive material on the substrate to form a telemetry coil. This step 804 can include forming two or more turns of the coil on the substrate. The telemetry coil can be formed on a single layer of the substrate or can be formed on or across multiple layers of the substrate. This step 804 can involve forming a single telemetry coil on the substrate. In some embodiments this step can involve forming the additional telemetry coils.

Step 806 involves forming an anatomy interface portion on the substrate. This step can involve disposing electrically conductive material on the substrate to form a portion of the component for interfacing with target anatomy, such as a stimulator portion (e.g., for providing electrical stimulation) or a sensor portion (e.g., for obtaining a measurement associated with a characteristic or property of target anatomy). This step can involve forming one or more electrodes on the substrate.

Step 808 involves forming electrical interface region on the substrate. This step can involve disposing electrically conductive material in the substrate to form an electrical interface region. The electrically conductive material can be disposed to form one or more pads, pins, or other electrically conductive regions to form the electrical interface. This step 808 can also involve connecting the electrical interface or components thereof to other portions of the monolithic component. For example, an electrically conductive pathway can be formed connecting an electrically conductive region of the electrical interface (e.g., a pad) to the anatomy interface portion (e.g., an electrode in the anatomy interface portion). In a further example, the anatomy interface portion can include multiple electrodes and there can be a portion of the electrical interface region associated with and electrically connected to each electrode such that an electronics module, when connected to the electrical interface region, can independently output stimulation to each of the electrodes. In some embodiments, discrete electronic components (e.g. integrated circuits, capacitors, and/or transistors) can be formed in the electrical interface region.

In addition to the foregoing steps, additional steps can also be made. For example, the process 800 can include disposing in electrically conductive trace linking one or more of the regions or portions thereof. It can also involve disposing one or more electrical components on the substrate. It can also include applying one or more additional layers of substrate or insulating material. The process can also involve treating curing forming shaping or otherwise modify the substrate and or formed portions in order to form the implantable medical component. The process can also involve cutting one or more components to form a particular shape. Importantly, it should be noted that the cited forming of the various regions can occur in any order and/or simultaneously in accordance with many embodiments of the invention. Note also that the above described processes can be implemented in any of a variety of suitable ways. For instance, the described processes can be implemented using known thin film deposition techniques, including those that are particularly compatible with the deposition of platinum. As mentioned previously, in some embodiments, an anatomy interface region comprises platinum; accordingly, in several embodiments, forming an anatomy interface portion on the substrate 806 comprises forming the anatomy interface portion using at least some platinum. Of course, to be clear, platinum can be included in any suitable region of a monolithic implantable medical device component in accordance with many embodiments of the invention. More generally, monolithic medical device components can include any of a variety of suitable materials in accordance with many embodiments of the invention.

Figure 9:
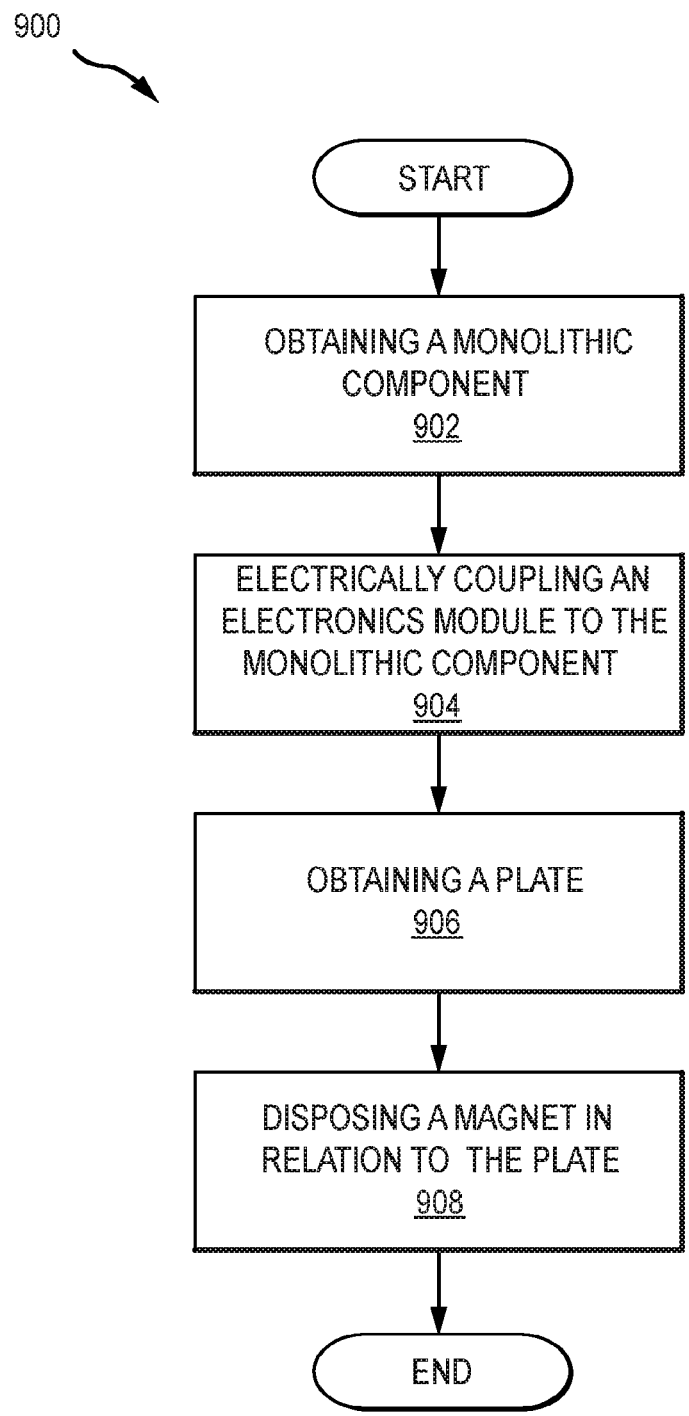
FIG. 9 illustrates an example process for manufacturing an implantable medical device in accordance with certain embodiments of the invention.

FIG. 9 illustrates an example process 900 for manufacturing an implantable medical device. The process 900 can begin with step 902, which involves obtaining a monolithic component. In some examples, this can involve receiving a premade monolithic component (e.g., monolithic component 300). In other examples, this can involve forming the monolithic component or a portion thereof (e.g., as described in relation to process 800).

Step 904 can follow step 902 and involves electrically coupling an electronics module to the monolithic component. This step 902 can involve obtaining an electronics module (e.g., a processing unit). The electronics module can include one or more electrically conductive portions coupleable with an electrical interface portion of the monolithic component. Electrically coupling the electronics module to the monolithic component can include connecting an electrical interface region of the monolithic component with a feedthrough of the electronics module. This can involve placing the feedthrough in electrical connection with a pad, pin, or other electrically conductive region of the monolithic component. In another example, an electrical pathway is formed by disposing the electronics module in direct contact with an electrically conductive region of the electrical interface region of the monolithic circuit board.

This step 904 can also include securing the electronics module and monolithic component in relation to each other. This can include soldering or otherwise attaching the electronics module to the monolithic component. In some examples, the electronics module and the monolithic component can be attached to a third component that anchors the two components in relation to each other (e.g., both the electronics module and the monolithic component can be disposed in a body material that holds the electronics module and monolithic component in relation to each other).

Step 906 involves obtaining a plate. This can including receiving a pre-made plate or forming a plate having one or more characteristics of plates described herein. This step 906 can further include disposing a portion of the monolithic component in relation to the plate. This can include disposing a portion of the monolithic component proximal a top, bottom, and/or side of the plate. This can include disposing a portion of the monolithic component circumferentially around the plate. This can include disposing a portion of the monolithic component in the plate. For example, the portion of the monolithic component can be a coil. The coil can be attached to a top portion, a bottom portion, and/or a side portion of the plate. Some or all of the coil can be embedded within the plate. This can include forming the plate or a portion thereof around the coil.

Step 908 involves disposing a magnet in relation to the plate. This can include obtaining a magnet, such as one disclosed herein, and disposing the magnet in relation to the plate such that the plate resists movement or rotation of the magnet. This can include disposing the magnet and the plate within a biocompatible body material of an implantable medical device, such that the magnet and the plate are proximate each other. In some embodiments, there can be more than one plate. In such embodiments, multiple plates can be obtained and the plates and the magnet can be disposed in relation to each other. For example, the magnet can be disposed between the first and second plate.

In some examples, the magnet can be disposed in relation to the plate such that the magnet is adapted to be separated from the plate or other components in a non-destructive way. For example, the magnet can be disposed within a cassette (e.g., as described in relation to medical device 700). The cassette can then be slid to a position proximate the plate to dispose the magnet within the cassette in relation to the plate.

In addition to the foregoing steps, additional steps can also be made. For example, the components (e.g., the plate, magnet, and coil) can be disposed within a material or housing. The material or housing can provide biocompatibility and protection to the components for implantation in a recipient. The body material can also help maintain a relative positioning of the components. In some examples, a recess or cavity can be formed in the body material into which the magnet and cassette can be slid. In this manner the magnet and cassette can be removed without damaging the body. The cassette can be kept in place with friction or a retention mechanism to retain its position until its removal is wanted.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and methods to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed:

1. An implantable medical device, comprising:
a monolithic implantable component, comprising:
a substrate comprising a telemetry coil region, an electrical interface region, and an elongate anatomy interface region;
a coil disposed within the substrate at the telemetry coil region;
one or more connectors formed on the electrical interface region, wherein the telemetry coil region extends from a first side of the electrical interface region in a first direction along an axis; and
a plurality of electrodes formed on the elongate anatomy interface region, wherein the plurality of electrodes is formed in a linear array, wherein the elongate anatomy interface region is configured as to be inserted into a cochlea of a recipient for positioning of the plurality of electrodes for stimulation of the recipient's auditory nerves from within the cochlea, and wherein the elongate anatomy interface region extends from a second side, opposite the first side, of the electrical interface region in a second direction, opposite the first direction, along the axis such that the telemetry coil region, the electrical interface region, and the elongate anatomy interface region are offset from one another along the axis; and
an electronics module external to the substrate, wherein the electronics module comprises a conductor configured to electrically connect to the one or more connectors of the monolithic implantable component.

2. The implantable medical device of claim 1, wherein the substrate comprises a second anatomy interface region, wherein the second anatomy interface region is separate from the elongate anatomy interface region and is electrically connected to the electrical interface region.

3. The implantable medical device of claim 2, further comprising:
at least one return electrode formed on the second anatomy interface region, wherein the at least one return electrode is in signal communication with the electrical interface region.

4. The implantable medical device of claim 1, wherein the elongate anatomy interface region and the electrical interface region are formed from one or more different materials.

5. The implantable medical device of claim 1, wherein the elongate anatomy interface region and the electrical interface region have different material properties.

6. The implantable medical device of claim 5, wherein the elongate anatomy interface region is more rigid than at least the electrical interface region to facilitate insertion of the elongate anatomy interface region into the cochlea.

7. The implantable medical device of claim 5, wherein the elongate anatomy interface region and the electrical interface region are treated differently to create differing material properties in the elongate anatomy interface region relative to the electrical interface region that facilitate insertion of the elongate anatomy interface region into the cochlea.

8. The implantable medical device of claim 5, wherein the elongate anatomy interface region and the electrical interface region comprise different numbers of material layers to create differing material properties in the elongate anatomy interface region relative to the electrical interface region that facilitate insertion of the elongate anatomy interface region into the cochlea.

9. The implantable medical device of claim 1, wherein the electronics module is disposed in a biocompatible housing.

10. The implantable medical device of claim 1, further comprising:
a plate; and
a magnet external to the substrate, wherein the magnet is disposed between the monolithic implantable component and the plate such that at least one of the monolithic implantable component and the plate restricts some rotational motion of the magnet.

11. An implantable medical device, comprising:
a telemetry coil disposed within a substrate;
an electrical interface region formed on the substrate, wherein the electrical interface region comprises segments that are offset from one another to form a space therebetween;
an anatomy interface region formed on the substrate, wherein the anatomy interface region includes one or more electrodes disposed thereon,
wherein the telemetry coil, the electrical interface region, and the anatomy interface region are integrated via the substrate; and
an electronics module external to the substrate, wherein the electronics module comprises a conductor configured to directly connect to the electrical interface region, and wherein the electronics module is configured to be positioned against the segments of the electrical interface region to be positioned over and extend across the space between the segments.

12. The implantable medical device of claim 11, wherein the substrate comprises a second anatomy interface region, wherein the second anatomy interface region is separate from the anatomy interface region and is electrically connected to the electrical interface region.

13. The implantable medical device of claim 11, wherein the anatomy interface region and the electrical interface region are formed from one or more different materials.

14. The implantable medical device of claim 11, wherein the anatomy interface region and the electrical interface region are treated differently to create differing material properties in the anatomy interface region relative to the electrical interface region.

15. The implantable medical device of claim 11, wherein the anatomy interface region and the electrical interface region comprise different numbers of material layers to create differing material properties in the anatomy interface region relative to the electrical interface region.

16. The implantable medical device of claim 11, further comprising:
a magnetic retention feature configured to permit a rotation of a magnet external to the substrate when the magnet is subjected to an externally-generated magnetic field;
the magnet external to the substrate.

17. The implantable medical device of claim 16, wherein the magnetic retention feature comprises at least one plate, and wherein the at least one plate is more rigid than a body material that houses the implantable medical device.

18. The implantable medical device of claim 16, further comprising a body material, wherein the magnetic retention feature includes the body material and a second component of the implantable medical device.

19. A method of manufacturing an implantable medical component comprising:
obtaining a substrate;
disposing a telemetry coil within the substrate;
forming an electrical interface region on the substrate, the electrical interface region extending from the telemetry coil in a direction along an axis;

forming an anatomy interface region on the substrate, the anatomy interface region extending from the electrical interface region in the direction along the axis such that the telemetry coil, the electrical interface region, and the anatomy interface region are offset from one another along the axis; and forming one or more electrodes on the anatomy interface region;

directly connecting an electronics module to the electrical interface region, wherein the electronics module is external to the substrate.

20. The method of claim 19, wherein directly connecting the electronics module to the electrical interface region comprises:

electrically coupling the electronics module to the electrical interface region, wherein the electronics module is configured to interact with the one or more electrodes based at least in part on a signal received at the telemetry coil.

21. The method of claim 19, further comprising:

forming a second anatomy interface region on the substrate, wherein the second anatomy interface region is separate from the anatomy interface region and is electrically connected to the electrical interface region.

22. The method of claim 19, further comprising:

treating the anatomy interface region and the electrical interface region differently to create differing material properties in the anatomy interface region relative to the electrical interface region.

23. The method of claim 19, further comprising:

forming the anatomy interface region and the electrical interface region with different numbers of material layers to create differing material properties in the anatomy interface region relative to the electrical interface region.

24. The method of claim 19, further comprising:

providing a magnet retention feature configured to permit a rotation of a magnet external to the substrate when the magnet is subjected to an externally-generated magnetic field; and providing the magnet in the magnet retention feature.

25. The method of claim 24, wherein the magnet retention feature comprises at least one plate.

* * * * *